(12) United States Patent
Palmskog et al.

(10) Patent No.: US 8,379,205 B2
(45) Date of Patent: *Feb. 19, 2013

(54) OPTICAL ARRANGEMENT FOR DETERMINING THE CONCENTRATION OF A SUBSTANCE IN A FLUID

(75) Inventors: Goran Palmskog, Jarfalla (SE); Fredrik Laurell, Danderyd (SE); Gunnar Elgcrona, Vallentuna (SE)

(73) Assignee: Mindray Medical Sweden AB, Sundbyberg (SE)

( * ) Notice: Subject to any disclaimer, the term of this patent is extended or adjusted under 35 U.S.C. 154(b) by 162 days.

This patent is subject to a terminal disclaimer.

(21) Appl. No.: 13/151,030

(22) Filed: Jun. 1, 2011

(65) Prior Publication Data
US 2011/0242538 A1    Oct. 6, 2011

Related U.S. Application Data

(63) Continuation of application No. 11/663,456, filed on Oct. 28, 2008, now Pat. No. 7,961,325.

(30) Foreign Application Priority Data

Sep. 23, 2004  (SE) ...................................... 0402292

(51) Int. Cl.
*G01N 21/00* (2006.01)
(52) U.S. Cl. ..................................................... 356/433
(58) Field of Classification Search .................. None
See application file for complete search history.

(56) References Cited

U.S. PATENT DOCUMENTS

| | | | |
|---|---|---|---|
| 5,245,410 A * | 9/1993 | Villuendas Yuste et al. .. | 356/445 |
| 6,556,306 B2 * | 4/2003 | Jiang et al. ..................... | 356/517 |
| 2002/0063866 A1 * | 5/2002 | Kersey et al. .................. | 356/478 |
| 2003/0052272 A1 * | 3/2003 | Kiuchi et al. ............. | 250/339.12 |
| 2003/0137669 A1 * | 7/2003 | Rollins et al. ................. | 356/479 |
| 2003/0176777 A1 * | 9/2003 | Muller-Dethlefs .......... | 600/322 |
| 2003/0218750 A1 * | 11/2003 | Friberg et al. ................. | 356/437 |
| 2004/0021100 A1 * | 2/2004 | Gouzman et al. ............. | 250/573 |

* cited by examiner

*Primary Examiner* — Gregory J Toatley
*Assistant Examiner* — Juan D Valentin, II
(74) *Attorney, Agent, or Firm* — Kory D. Christensen; Stoel Rives LLP

(57) ABSTRACT

An arrangement for determining concentration of substances in a fluid comprising a light source for generating primary light pulses within a wavelength interval, a light pulse splitter adapted to split up the primary light pulses into a predetermined number of secondary light pulses to be transmitted through the fluid, the secondary light pulses being separated in time as well as wavelength to be differently absorbed upon passage of the fluid depending on the concentration of the substances, a detector for detecting intensity of the differently absorbed secondary light pulses, and a comparator for comparing the intensities of the differently absorbed secondary light pulses with different reference intensities corresponding to different substances to thereby determine the concentration of the substances in the fluid.

12 Claims, 2 Drawing Sheets

OPTICAL ARRANGEMENT FOR DETERMINING THE CONCENTRATION OF A SUBSTANCE IN A FLUID

TECHNICAL FIELD

The invention relates to an arrangement for determining concentration of at least one substance in a fluid.

BACKGROUND OF THE INVENTION

There are many situations in which it is necessary to be able to determine and monitor the concentration of a substance in a fluid. One such situation is e.g. narcosis where five different anesthetic gases are administered in different combinations and mixtures to the respiratory circuit of a patient. In that case, it is of utmost importance that the concentration, i.e. the dose of the respective gas is kept under strict control.

FR 2 677 120 (Bussotti) discloses an arrangement for photometric spectroscopy, wherein measurements may be carried out on remote samples by using fibre optics. According to the Bussotti arrangement, the light from a lamp passes through an optical chopper that consists of a motor driven rotating disc with apertures which control light entry into the ends of two optical fibres. The two optical fibres illuminate a reference and a test sample, respectively. The output is recombined into a single optical fibre, for instance by the use of mirrors, for transmission to a measuring unit. Even though the arrangement described in FR 2 677 120 may be effective in many ways, the measuring principles are clearly different from the ones of the present invention, which will be described in greater detail herein below. With the Bussotti arrangement there is also a need for the illumination of a separate reference sample. According to the arrangement of the present invention, there is no need for such a reference sample but the reference measuring means are instead according to a preferred embodiment, in an effective way integrated within the optics of the arrangement.

The arrangement of the present invention can also be manufactured at low costs without having to sacrifice the high functionality and high measurement accuracy of the arrangement, especially with use of fibre optics.

SUMMARY OF THE INVENTION

The object of the invention is to provide an improved arrangement for determining concentration of at least one substance in a fluid, e.g. a specific gas in a gas mixture.

This object is achieved with an arrangement according to the independent claims with preferred embodiments set forth in the dependent claims.

BRIEF DESCRIPTION OF THE DRAWING

The invention will be described more in detail below with reference to the appended drawing on which

DESCRIPTION OF THE INVENTION

Figure 1:
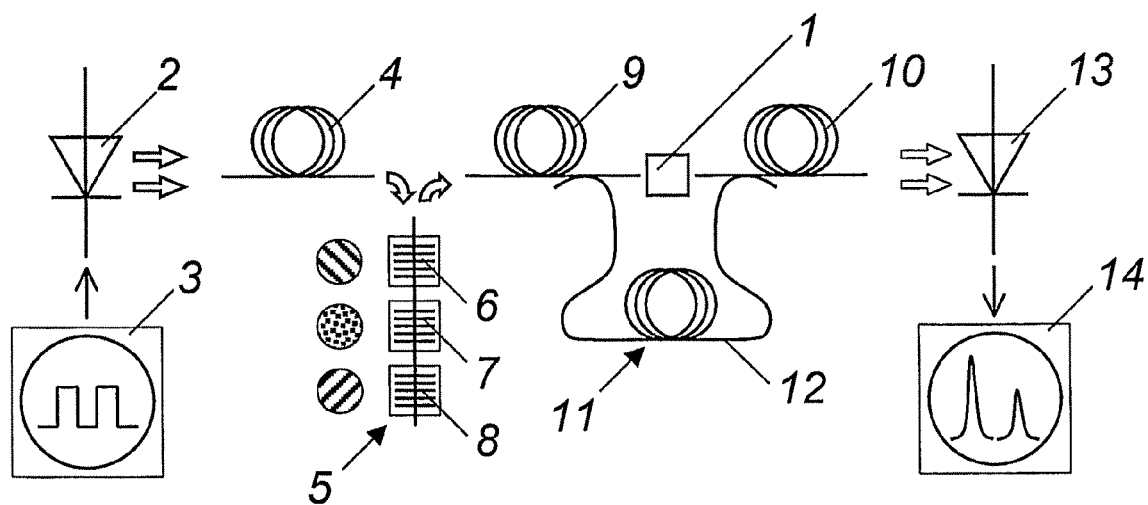
FIG. 1 is a schematic illustration of a first embodiment of an arrangement according to the invention.

FIG. 1 is a schematic illustration of a first embodiment of an arrangement according to the invention for determining concentration of at least one substance in a fluid.

In the embodiment in FIG. 1, the fluid is a gas mixture that comprises three different, known gases, the concentration of which is to be determined. It is to be understood that the invention is not restricted to determining concentration of just gases but can be applied to any fluid including liquids. It is also to be understood that the invention in no way is limited to determine the concentration of three known gases, but that any number of gases comprised in the gas mixture can be determined. Naturally, this is true also for the embodiment of the present invention described in connection with FIG. 3.

In FIG. 1, the fluid, i.e. the gas mixture, is located in a measuring cell 1, e.g. a flow cell, but it is to be understood that the fluid does not necessarily have to be restricted to a measuring cell but the fluid can also be present in the free space.

In accordance with the invention, the measuring cell can also be a hollow fibre.

In the embodiment in FIG. 1, a light source 2 is controlled by a pulse generator 3 to generate primary light pulses. The light source 2 can be a broadband light source, e.g. a superluminescent LED. The pulse generator (3) is to be understood as any pulse generating means adapted to generate primary light pulses from the light source. The person skilled in the art can easily choose between known pulse generating means in order to accomplish the above described. The pulse generating means can thus for instance be incorporated into or integrated with the light source.

The primary light pulses are generated within a wavelength interval that in this embodiment comprises three different predetermined wavelengths $\lambda_1$, $\lambda_2$ and $\lambda_3$ that are known to be absorbed by the respective known gases in the gas mixture.

Figure 2A:
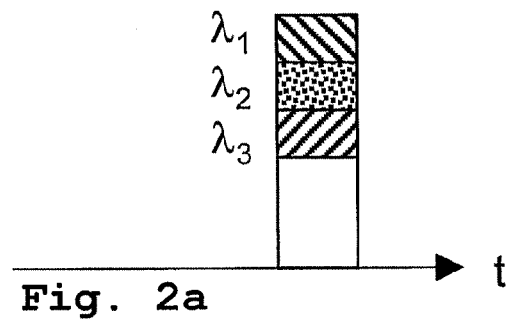
FIGS. 2a-d illustrate light pulses in different points of the embodiment in FIG. 1.

One such primary light pulse outputted by the light source 2 is illustrated in FIG. 2a.

If primary light pulses within more than one wavelength interval is needed, e.g. in order to be able to detect a large number of different substances, it is to be understood that a light source that is able to generate primary light pulses within more than one wavelength interval can be used. As an alternative, a number of different light sources can be used.

In accordance with the invention, in the embodiment in FIG. 1, the light source 2 is coupled via an optical fibre 4 and e.g. a fibre optical circulator or a fibre optical coupler indicated by two arrows in FIG. 1 to an input terminal of a light pulse splitter 5.

The light pulse splitter 5 in the embodiment in FIG. 1 comprises three fibre Bragg gratings 6, 7, 8 that each has a predetermined reflection wavelength corresponding to the respective wavelength $\lambda_1$, $\lambda_2$ and $\lambda_3$ of the primary light pulses generated by the light source 2. The light pulse splitter 5 is terminated by a low reflection termination (not shown). The light pulse splitter 5 splits up the primary light pulses into a predetermined number of secondary light pulses thus corresponding to the predetermined wavelengths,—in the embodiment in FIG. 1 into three secondary light pulses—that are separated in time as well as wavelength.

Figure 2B:
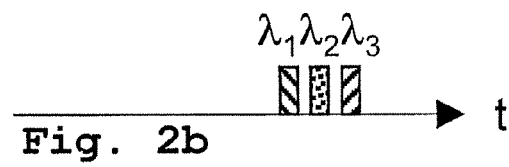
Figure 2C:
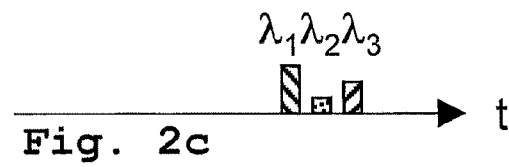

The three secondary light pulses illustrated in FIG. 2b that have respective wavelengths $\lambda_1$, $\lambda_2$ and $\lambda_3$ are coupled from an output terminal of the light pulse splitter 5 via the fibre optical circulator or the fibre optical coupler to an input end of an optical fibre 9. From the output end of the optical fibre 9, the three secondary light pulses in FIG. 2b are transmitted through the measuring cell 1 to be differently absorbed upon passage of the gas mixture depending upon the concentration of the respective gas. The three differently absorbed secondary light pulses illustrated in FIG. 2c are received by an input end of an optical fibre 10. Moreover, if necessary for calibration purposes, the three secondary light pulses in FIG. 2b are coupled from the output end of the optical fibre 9 to an input terminal of a reference light pulse generating device 11 that in the embodiment in FIG. 1 comprises an optical delay loop in the form of an optical fibre 12. The delay loop, i.e. the optical fibre 12 can comprise a wavelength filter or a fibre grating structure (not shown) corresponding to the wavelengths of all different gases to be measured.

Figure 2D:
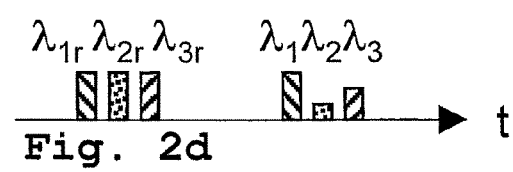

The output terminal of the reference light pulse generating device 11, i.e. the output end of the optical fibre 12, is coupled to the input end of the optical fibre 10. In response to the three secondary light pulses in FIG. 2b, the reference light pulse generating device 11 generates three delayed reference light pulses associated with the respective secondary light pulse, i.e. having the same predetermined wavelengths, and having reference intensities. In FIG. 2d, the three delayed reference light pulses are denoted $\lambda_{1r}$, $\lambda_{2r}$ and $\lambda_{3r}$.

Depending on the length and/or the configuration of the optical fibre 12, the delayed reference light pulses can be generated at any point in time provided that a delayed reference light pulse is generated at a point in time that is later than its respective secondary light pulse, i.e. the secondary light pulse having the same predetermined wavelength. Thus, for instance in FIG. 2d, the light pulse denoted $\lambda_{3r}$ can be comprised in between $\lambda_3$ and $\lambda_2$ and is not restricted to be generated after $\lambda_1$. This is something the skilled person readily appreciates.

The three differently absorbed secondary light pulses $\lambda_1$, $\lambda_2$ and $\lambda_3$ and the three associated delayed reference light pulses $\lambda_{1r}$, $\lambda_{2r}$ and $\lambda_{3r}$ are coupled from the output end of the fibre 10 to an input terminal of a detector 13, e.g. a photodiode, for detecting the intensity of all incoming light pulses. A comparator 14 is connected to an output terminal of the detector 13 for comparing the intensities of the differently absorbed secondary light pulses with the intensities of the respective associated reference light pulses to thereby determine the concentration of the respective gas in the gas mixture in the measuring cell 1.

Figure 3:
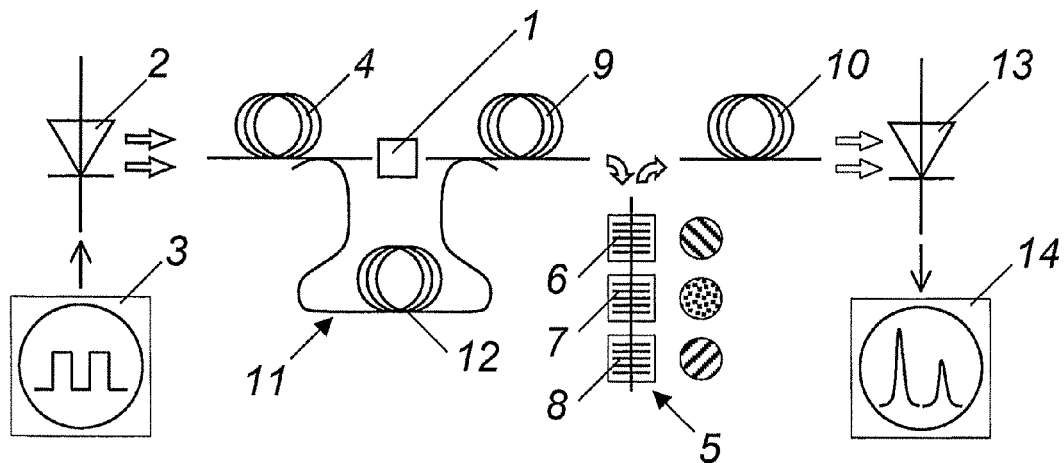
FIG. 3 is a schematic illustration of a second embodiment of an arrangement according to the invention.

FIG. 3 is a schematic illustration of a second embodiment of an arrangement according to the invention. In FIG. 3, all components are identical to the components in FIG. 1 but located differently and have therefore been provided with the same reference numerals. The embodiment in FIG. 3 differs from the embodiment in FIG. 1 mainly in that the light pulse splitter 5 is located after the measuring cell 1 instead of before it. In the embodiment in FIG. 3 as in the embodiment in FIG. 1, the light source 2 is coupled to an input end of an optical fibre 4.

Figure 4A:
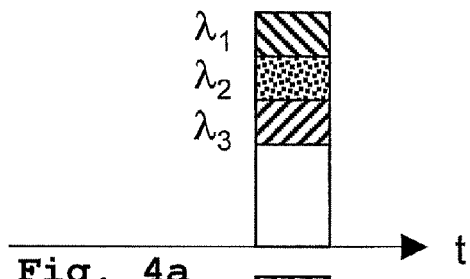
FIGS. 4a-d illustrate light pulses in different points of the embodiment in FIG. 3.

However, from the output end of the optical fibre 4, the primary light pulses generated by the light source 2 comprising the predetermined wavelengths—one such primary light pulse being illustrated in FIG. 4a—are directly transmitted through the measuring cell 1 to be differently absorbed upon passage of the gas mixture depending upon the concentration of the respective gas.

Figure 4B:
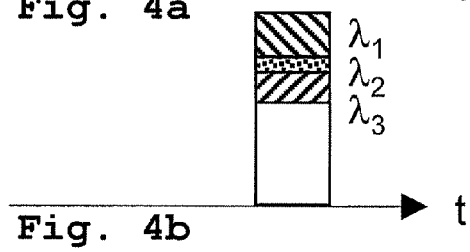

The differently absorbed primary light pulses—one being illustrated in FIG. 4b—are received by the input end of the optical fibre 9. Also, from the output end of the optical fibre 4 in FIG. 3, the primary light pulses in FIG. 4a generated by the light source 2, if necessary for calibration purposes, are coupled to the input terminal of the reference light pulse generating device 11 that also in the embodiment in FIG. 3 comprises the optical delay loop in the form of an optical fibre 12. Also in this case, the delay loop, i.e. the optical fibre 12, can comprise a wavelength filter or a fibre grating structure corresponding to the wavelengths of all different gases to be measured.

The output terminal of the reference light pulse generating device 11, i.e. the output end of the optical fibre 12, is coupled to the input end of the optical fibre 9. In FIG. 3, the output end of the fibre 9 is coupled via e.g. a fibre optical circulator or a fibre optical coupler indicated by two arrows to the light pulse splitter 5 that also in this case comprises the three fibre Bragg gratings 6, 7, 8 that each has a predetermined reflection wavelength corresponding to the respective wavelength $\lambda_1$, $\lambda_2$ and $\lambda_3$ of the first set of primary of light pulses generated by the light source 2 and the delayed or the second set of primary light pulses generated by the reference light pulse generating device 11.

Figure 4C:
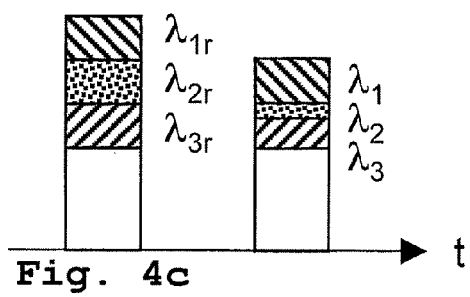

In FIG. 4c, the delayed second set of primary light pulses, for purpose of illustration only, are shown as including reference wavelengths $\lambda_{1r}$, $\lambda_{2r}$ and $\lambda_{3r}$. It is however to be understood that wavelengths $\lambda_{1r}$, $\lambda_{2r}$ and $\lambda_{3r}$ and wavelengths $\lambda_1$, $\lambda_2$ and $\lambda_3$ are the same. Depending on the length and/or the configuration of the optical fibre 12, the delayed reference light pulses can be generated at any point in time provided that the delayed second set of reference light pulses is generated at a point in time that is later than the first set of primary light pulses.

Figure 4D:
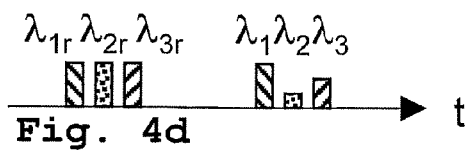

As in the embodiment in FIG. 1, the light pulse splitter 5 in FIG. 3 is terminated by a low reflection termination. The light pulse splitter 5 splits up the differently absorbed first set of primary light pulses and the delayed second set of primary light pulses into three differently absorbed secondary light pulses and three associated reference light pulses, i.e. having the same predetermined wavelengths and having reference intensities, that are all separated in time as well as wavelength as illustrated in FIG. 4d.

The three differently absorbed secondary light pulses and the three associated delayed reference light pulses, all having respective predetermined wavelengths $\lambda_1$, $\lambda_2$ and $\lambda_3$ are coupled via the output terminal of the light pulse splitter 5 to the input end of the optical fibre 10.

As in the embodiment in FIG. 1, the three differently absorbed secondary light pulses and the three associated delayed reference light pulses are coupled from the output end of the fibre 10 to the input terminal of the detector 13 for detection of the intensity of all incoming light pulses.

The comparator 14 is connected to the output terminal of the detector 14 for comparing the intensities of the differently absorbed secondary light pulses with the intensities of the respective associated delayed reference light pulses to determine the concentration of the respective gas in the gas mixture in the measuring cell 1.

It will be understood that the invention is not restricted to the above-described exemplifying embodiments thereof and that several conceivable modifications of the invention are possible within the scope of the attached claims. For instance in the description text of the present invention, where reference is made to an optical fibre 4,9,10 or 12, respectively, it is to be understood that any of these optical fibres just as well can comprise several fibres, provided separately or in a bunch.

The invention claimed is:

1. A system for determining a concentration of at least one substance in a fluid, the system comprising:
   a pulsed light source to generate a first light pulse comprising at least one predetermined wavelength that is absorbed differently in the fluid depending on the concentration of the substance;
   a light pulse splitter to receive the first light pulse from the pulsed light source and to split the first light pulse into at least a second light pulse and a third light pulse, the second light pulse comprising the at least one predetermined wavelength, the second light pulse and the third light pulse being separated in time as well as wavelength, wherein the second light pulse and the third light pulse pass through the fluid along a first light path such that the substance in the fluid partly absorbs the second light pulse;

a reference light pulse generating device to generate at least one reference intensity that bypasses the fluid along a second light path without passing through a reference sample, the at least one reference intensity comprising the at least one predetermined wavelength and having a delay in time relative to the partly absorbed second light pulse;

a detector to detect the intensity of the partly absorbed second light pulse and the at least one reference intensity; and a comparator to compare the detected partly absorbed second light pulse with the detected at least one reference intensity to thereby determine the concentration of the at least one substance in the fluid.

2. The system of claim 1, wherein the light pulse splitter is interconnected between optical fibers by one of a fiber optical circulator and an optical coupler.

3. The system of claim 1, wherein the reference light pulse generating device comprises an optical fiber.

4. The system of claim 1, wherein the light pulse splitter comprises at least one fiber Bragg grating for reflecting the at least one predetermined wavelength.

5. The system according to claim 4, wherein the at least one fiber Bragg grating is terminated by a low reflection termination.

6. The system of claim 1, further comprising a measuring cell for the fluid to pass through, the measuring cell comprising a hollow fiber.

7. A system for determining a concentration of at least one substance in a fluid, the system comprising:

a pulsed light source to generate a first light pulse comprising at least one predetermined wavelength that passes through the fluid along a first light path and is absorbed differently in the fluid depending on the concentration of the substance such that the fluid partly absorbs the first light pulse;

a reference light pulse generating device to generate at least one reference intensity from the pulsed light source that bypasses the fluid along a second light path without passing through a reference sample, the at least one reference intensity comprising the at least one predetermined wavelength and having a delay in time relative to the partly absorbed first light pulse;

a light pulse splitter to receive the partly absorbed first light pulse and to split the partly absorbed first light pulse into at least a second light pulse and a third light pulse, the second light pulse comprising the at least one predetermined wavelength, the second light pulse and the third light pulse being separated in time as well as wavelength;

a detector to detect the intensity of the second light pulse and the at least one reference intensity; and a comparator to compare the detected second light pulse with the detected at least one reference intensity to thereby determine the concentration of the at least one substance in the fluid.

8. The system of claim 7, wherein the light pulse splitter is interconnected between optical fibers by one of a fiber optical circulator and an optical coupler.

9. The system of claim 7, wherein the reference light pulse generating device comprises an optical fiber.

10. The system of claim 7, wherein the light pulse splitter comprises at least one fiber Bragg grating for reflecting the at least one predetermined wavelength.

11. The system of claim 10, wherein the at least one fiber Bragg grating is terminated by a low reflection termination.

12. The system of claim 7, further comprising a measuring cell for the fluid to pass through, the measuring cell comprising a hollow fiber.

* * * * *